United States Patent [19]

Stretanski et al.

[11] 4,064,106

[45] Dec. 20, 1977

[54] POLYMERS STABILIZED BY ESTERS OF PHOSPHINODITHIOIC ACIDS

[75] Inventors: Joseph Anthony Stretanski, Clinton; Vincent Gerard Grosso, Piscataway, both of N.J.

[73] Assignee: American Cyanamid Company, Stamford, Conn.

[21] Appl. No.: 635,184

[22] Filed: Nov. 25, 1975

[51] Int. Cl.$^2$ .............................................. C08K 5/50
[52] U.S. Cl. ...................... 260/45.95 C; 260/45.7 PS; 260/45.9 KA; 260/45.95 N; 260/958; 260/961
[58] Field of Search ................ 260/45.7 PS, 45.95 C, 260/953, 958, 961, 928, 930; 252/46.6

[56] References Cited

U.S. PATENT DOCUMENTS

| | | | |
|---|---|---|---|
| 2,266,514 | 12/1941 | Romieux et al. | 260/928 |
| 2,665,294 | 1/1954 | Kosolapoff | 252/46.6 |
| 3,281,505 | 10/1966 | Spivack | 260/953 |
| 3,293,208 | 12/1966 | Milionis et al. | 260/45.75 |
| 3,296,193 | 1/1967 | Walsh et al. | 260/45.75 |
| 3,475,370 | 10/1969 | Giolito | 260/45.7 |
| 3,492,373 | 1/1970 | Matson et al. | 260/928 |
| 3,534,127 | 10/1970 | Spivack | 260/968 |
| 3,705,216 | 12/1972 | Farley | 260/970 |
| 3,742,096 | 6/1973 | Spivack | 260/953 |
| 3,753,945 | 8/1973 | Kleiner | 260/45.85 H |
| 3,763,287 | 10/1973 | Chiddix et al. | 260/941 |
| 3,801,543 | 4/1974 | Meltsner | 260/45.95 |
| 3,951,912 | 4/1976 | Susi | 260/45.85 |

*Primary Examiner*—Donald E. Czaja
*Assistant Examiner*—R. A. White
*Attorney, Agent, or Firm*—Frank M. Van Riet

[57] ABSTRACT

This invention relates to polymer compositions containing light stabilizing amounts of an ester of a phosphinodithioic acid.

26 Claims, No Drawings

POLYMERS STABILIZED BY ESTERS OF PHOSPHINODITHIOIC ACIDS

This invention relates to light stabilizing compounds for thermoplastic polymers. More particularly, this invention relates to polyolefin compositions stabilized against the deteriorative effects of ultraviolet light containing an effective amount of an ester of a phosphinodithioic acid. This invention also relates to methods for stabilizing thermoplastic polymers against the deteriorative effects of ultraviolet light by incorporating in the unstabilized polymer an effective amount of an ester of a phosphinodithioic acid.

It is well known that sunlight and other sources of ultraviolet radiation cause degradation of polymers as evidenced by embrittlement or yellowing of plastic articles made therefrom.

It is also well known that this degradation can be inhibited by the use of ultraviolet light stabilizers incorporated in or on such articles.

The use of the ammonium salt of dicyclohexylphosphinodithioic acid to impart light stability to polyolefins is disclosed by Milionis et al in U.S. Pat. No. 3,293,208,. Continuing efforts are being made to discover light stabilizers which will be superior to those currently available.

We have discovered that compounds of the formula:

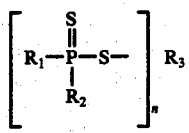
(I)

wherein $R_1$ and $R_2$ are selected from alkyl, cycloalkyl, substituted alkyl, substituted and unsubstituted aryl and aralkyl, and $n$ is 1 or 2, provided that when $n$ is 1, $R_3$ is selected from alkyl, cycloalkyl, substituted alkyl, alkylthioalkyl, substituted and unsubstituted aralkyl, aryl and aralkylthioalkyl, and when $n$ is 2, $R_3$ is selected from alkylene, hydroxyalkylene, oxybis and thiobis (alkylene) and substituted and unsubstituted arylene, are effective in stabilizing thermoplastic polymers against the deteriorative effects of ultraviolet light.

Within the general class of the compounds of formula (I) the preferred stabilizer compounds include those represented by the formula:

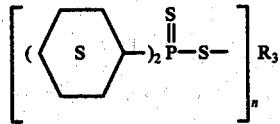
(II)

wherein $n$ and $R_3$ have the same meanings as in formula (I).

Especially preferred, because they give the best light stability to polyolefins, are the stabilizer compounds represented by the formula:

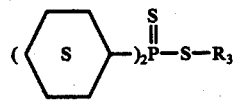
(III)

wherein $R_3$ is alkyl of 1–18 carbon atoms.

Within the broad class of esters represented by the general formula:

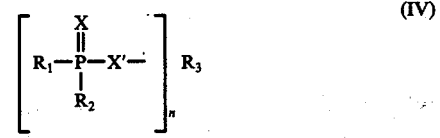
(IV)

wherein $R_1$, $R_2$ and $R_3$ represent organic moities previously defined, X and X' are independently oxygen or sulfur, and $n$ is 1 or 2 we have discovered stabilizer compounds represented by formulas (I), (II) and (III), above, which have certain structural features in common. First, both X and X' of formula (IV) must be sulfur. Compounds wherein either X or X', or both X and X', are oxygen are inferior or inoperative as light stabilizers in polyolefins. Secondly, $R_3$ in formula (IV) must not be aromatic since compounds wherein $R_3$ is aromatic are inferior light stabilizers for polyolefins. Thirdly, if $R_3$ is aralkyl, ardialkylene, aralkylthioalkyl, or arylthioalkyl the aryl segment must be monocyclic.

The compounds of formulas (I), (II), and (III), above, when incorporated in thermoplastic polymers, such as unstabilized general purpose polyolefins, significantly inhibit degradation of the polymer due to exposure to light. Other advantages of the stabilizer compounds of this invention are as follows:

1. The compounds of this invention do not impart a color to the stabilized material.
2. The compounds of this invention are especially advantgeous in heavily pigmented polyolefins wherein the conventional ultraviolet absorbers, such as 2-hydroxy-4-n-octyloxybenzophenone, lose their stabilizing capacity; and
3. The compounds of this invention are free-flowing and therefore easy to handle.

DESCRIPTION OF PREFERRED EMBODIMENTS

As employed herein the term "alkyl" is defined as a hydrocarbon radical, containing from 1 to 18 carbon atoms, either straight or branched chain; "cycloalkyl" is defined as a cyclic saturated hydrocarbon radical containing 5 or 6 carbon atoms; "substituted alkyl" is defined as a straight or branched chain hydrocarbon radical substituted with one or more hydroxyl, alkoxy, cyano groups or halogen atoms selected from chloro, bromo, or fluoro.

As employed herein the terms "substituted and unsubstituted aryl and aralkyl" refer to radicals having the formulas (V) and (VI), respectively,

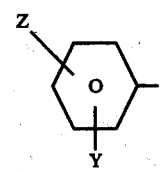
(V)

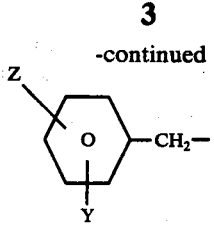

wherein Y and Z are selected from hydrogen, lower alkyl, lower alkoxy, hydroxy or halogen; "lower alkyl" and "lower alkoxy", as employed herein, mean a straight or branched chain hydrocarbon radical containing 1 to 8 carbon atoms and a straight or branched chain alkoxy group containing 1 to 8 carbon atoms, respectively.

The term "alkylthioalkyl" as employed herein is defined as a radical of the formula:

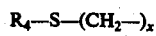

(VII)

wherein $R_4$ is lower alkyl and X is 1 to 18.

The terms "substituted and unsubstituted aryl- and aralkyl-thioalkyl" refer to radicals of the formulas (VIII) and (IX), respectively,

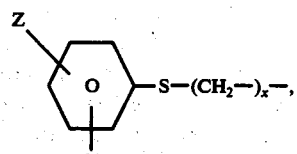

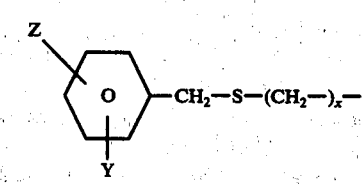

wherein Y, Z and X are as defined above.

The term "alkylene" as used herein is defined as a bivalent straight, or branched-chain hydrocarbon radical containing 1 to 18 carbon atoms.

The terms "thiodialkylene" and "oxydialkylene" as employed herein are defined as bivalent radicals of the formulas (X) and (XI), respectively,

wherein y and z are independent integers from 1 to 8.

The term "ardialkylene" as employed herein is defined as a radical of the formula:

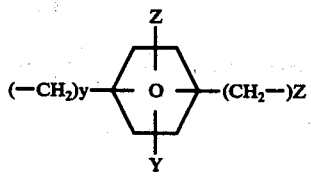

wherein Y and Z are as previously defined and y and z are independent integers from 1 to 8.

Compounds within the scope of formula (I) can be prepared in several ways. In one procedure the ammonium salt of a phosphinodithioic acid of formula (XIII) in which $R_1$ and $R_2$ are as defined above, is reacted with an equimolar amount of an alkyl bromide of formula (XIV) in refluxing acetone to obtain the desired product of formula (XV). The reaction may be written as follows:

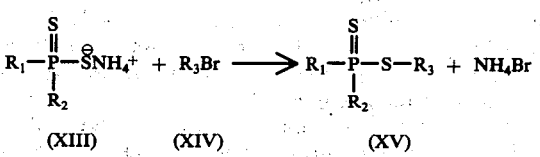

Diesters within the scope of formula (I) can be prepared similarly using 2 moles of (XIII) per mole of a suitable dihalide. Other procedures for the preparation of compounds of formula (I) are described in chapter 14 of "Organic Phosphorous Compounds" (1973) by Kosalopoff and Moier, and U.S. Pat. No. 3,232,830 and 3,705,216, both of which are hereby incorporated herein by this reference thereto.

Illustrative examples of monoesters of formula (I) within the purview of this invention are the following: methyl dicyclohexylphosphinodithioate; n-butyl dicyclohexylphosphinodithioate; n-octyl dicyclohexylphosphinodithioate; 2-hydroxyethyl dicyclohexylphosphinodithioate; cyclohexyl dicyclohexylphosphinodithioate; benzyl dicyclohexylphosphinodithioate; 2-cyanoethyl dicyclohexylphosphinodithioate; 2,6-dimethyl-3-hydroxy-4-t-butylbenzyl dicyclohexylphosphinodithioate; 3,5-di-t-butyl-4-hydroxybenzyl dicyclohexylphosphinodithioate; s-ethylmercaptomethyl dicyclohexylphosphinodithioate; s-phenylmercaptomethyl dicyclohexylphosphinodithioate; s-benzylmercaptomethyl dicyclohexylphosphinodithioate; s-ethylmercaptoethyl dicyclohexylphosphinodithioate; n-butyl diisobutylphosphinodithioate; 2-hydroxyethyl di-n-butylphosphinodithioate; methyl dimethylphosphinodithioate; methyl dioctadecylphosphinodithioate; n-butyl n-butylcyclohexylphosphinodithioate; n-octyl bis(2-cyanoethyl)phosphinodithioate; n-octadecyl dibenzylphosphinodithioate; n-butyl diphenylphosphinodithioate; n-butyl cyclohexylphenylphosphinodithioate; and n-octodecyl dicyclohexylphosphinodithioate.

Illustrative examples of diesters of formula (I) within the purview of this invention are the following: methylenebis(dicyclohexylphosphinodithioate); 1,2-ethylenebis-(dicyclohexylphosphinodithioate); 1,3-propylenebis(dicyclohexylphosphinodithioate); 1,10-decamethylenebis(dicyclohexylphosphinodithioate); 1,18-octadecamethylenebis(dicyclohexylphosphinodithioate); 2-hydroxy-1,3-propylenebis(dicyclohexylphosphinodithioate); thiodimethylenebis(dicyclohexylphosphinodithioate); 2,2'-thiodiethylenebis(dicyclohexylphosphinodithioate); 6,6'-thiodihexamethylenebis(dicyclohexylphosphinodithioate); oxydimethylenebis(dicyclohexylphosphinodithioate); 2,2'-oxydiethylenebis(dicyclohexylphosphinodithioate); 6,6'-oxydihexamethylenebis(dicyclohexylphosphinodithioate); 8,8'-thiodioctamethylenebis(dicyclohexylphosphinodithioate); 8,8'-oxydioctamethylenebis(dicyclohexylphosphinodithioate); 1,4-xylylenebis(dicyclohexylphosphinodithioate); 1,2-xylylenebis(dicyclohexylphosphinodithioate); methylenebis-(cyclohexylethylphosphinodithioate); methylenebis(dibenzylphosphinodithioate); 1,18-octadecamethylenebis(dibenzylphosphinodithioate); 1,2-ethylenebis(benzylcyclohexylphosphinodithioate); 2,2'-thiodiethylenebis(din-propylphosphinodithioate); 2,2'-thiodiethylenebis(dibenzylphosphinodithioate); 1,3-propylenebis(cyclohexylphenylphosphinodithioate); 1,18-octadecamethylenebis(diphenylphosphinodithioate); 2,2'-thiodiethylenebis(diphenylphosphinodithioate); 6,6'-thiodihexametnhylenebis(cyclohexylethylphosphinodithioate); oxydimethylenebis(diphenylphosphinodithioate); 2,2'-oxydiethylenebis(dibenzylphosphinodithioate); 6,6'-oxydihexamethylene-(di-n-propylphosphinodithioate); and 8,8'-thiodioctamethylenebis(cyclohexylpropylphosphinodithioate).

Plastic materials which are stabilized against degradation by ultraviolet light using these compounds include polyvinyl chloride, polyvinylidene chloride, copolymers of vinyl chloride and vinylidene chloride, polystyrene, polyesters, cellulose acetate, polyvinyl acetate, polyvinyl fluoride, and polymethyl methacrylate. They are particularly useful in polyolefins, such as polyethylene and polypropylene. These compounds may be incorporated in or on such plastic materials by any of the various standard procedures known in the art for such purpose, such as by dry blending the additive with the polymer in powder or granular form followed by molding or extruding; by milling; by immersing the polymer as film, sheet, fibers, etc. in a solution of the additive in an appropriate solvent (as in a dye process); etc.

The plastic material should contain an effective light stabilizing amount of the compound of formula (I), which amount will depend on the nature of the plastic and the amount of exposure to ultraviolet light to which the plastic will be subjected. Generally, an amount between about 0.1% and 5% by weight of plastic will be found satisfactory and between about 0.2% and 2% will be preferred. The compound of formula (I) may be used in the plastic alone or in combination with other additives, such as fillers, antioxidants, flame retardants, heat stabilizers, anti-slipping and anti-static agents, supplemental light stabilizers, pigments, dyes, lubricants, etc.

While it is not required that other additives must be included to obtain the desired stabilization, as mentioned previously, other additives may be included. Such additional additives may be used in the range of 0.1% to 2% by weight on the weight of the polymer.

Illustrative of suitable antioxidants are those of the hindered phenol type such as: 2,6-di-t-butyl-p-cresol; 4,4'-bis(2,6-di-t-butylphenol); 4,4'-bis(2,6-di-iso-propylphenol); 2,4,6-tri-t-butylphenol; 2,2'-thiobis(4-methyl-6-6-butylphenol); and octadecyl 2(3',5'-di-t-butyl-4'-hydroxyphenyl-propionate; etc.; esters of thiodipropionic acid, such as: dilaurylthiodipropionate; and distearylthiodipropionate; etc.; hydrocarbyl phosphites, such as: triphenyl phosphite; trinonyl phosphite; and diphenyldecyl phosphite; etc.; and combinations thereof.

Illustrative of the supplemental light stabilizers are those of the benzotriazole class, such as: 2-(2'-hydroxy-5'-methylphenyl)benzotriazole; and 2-(2'-hydroxy-3',5'-di-t-butylphenyl)-5-chlorobenzotriazole; those of the 2-hydroxy-4-methoxybenzophenone type, such as: 2-hydroxy-4-methoxybenzophenone; 2-hydroxy-4-octyloxybenzophenone; and 2,2'-dihydroxy-4,4'-dimethoxybenzophenone; hindered phenol esters, such as: 2',4'-di-t-butylphenyl-3,5-di-t-butyl-4-hydroxybenzoate; metal complexes, such as: nickel complexes of 2,2'-thiobis(4-t-octylphenol); nickel butylamine complex of 2,2'-thiobis(4-t-octylphenol); nickel complexes of bis(4-t-octylphenyl)sulfone; nickel dibutyl dithiocarbamate; and nickel salts of 4-hydroxy-3,5-di-t-butylbenzyl; phosphonic acid monoalkyl esters where alkyl is methyl ethyl, propyl, butyl, etc.; and nickel complex of 2-hydroxy-4-methylphenyl-undecyl ketone oxime, etc.

Further illustrative examples of suitable antioxidants and of suitable supplemental light stabilizers can be found in U.S. Pat. No. 3,488,920 and 3,496,134.

The polyolefins used herein are general purpose unstabilized materials, such as polyethylene and polypropylene, which may also contain samll amounts of a processing antioxidant, such as 2,4,6-tri-t-butylphenol.

The instant invention is further illustrated by the following examples which are not limitative thereof. Parts and percentages shown therein are by weight unless otherwise indicated. An asterisk means that the data presented is an average of two tests.

EXAMPLE 1

(R 8664-56-1)

Preparation of n- Octadecyl Dicyclohexylphosphinodithioate

To 14.0 g. (0.05 m.) of the ammonium salt of dicyclohexylphosphinodithioic acid in 250 mls. of acetone was added 16.67 g. (0.05 m.) of n-octadecylbromide and the mixture was refluxed for 15 hours. The precipitate was then separated by filtration and the filtrate was cooled to precipitate a crystalline solid. The crystalline material was filtered off and recrystallized from acetone to obtain 20 g. (77.8% yield) of product which melted at 67°–69° C.

EXAMPLE 2

Testing in Polypropylene

The phosphinodithioic acid ester of Example 1 was dry blended with a mastermix of unstabilized general purpose polypropylene (Profax ® 6401), containing 0.2% by weight of a processing antioxidant, 2,4,6-tritertiarybutyl phenol, at a concentration of 0.5%, based on the weight of the polyolefin. The blend was milled at 350°–370° F for 5 minutes and the milled sample was compression molded at 400° F into films 4–5 mils thick. The compression molded film and a control film, identically prepared without the light stabilizer compound, were exposed in a 6000 Watt Xenon Arc Weather-O-Meter (Atlas Electric Devices Company, Chicago, Ill.) Model 60WR until structural failure occurred. A sample was considered to have failed when the carbonyl content of the infrared spectrum of the exposed film reached 0.1% by weight, a generally accepted point of embrittlement. The test sample containing the ester of Example 1 lasted 600 hours longer than the control. The total number of hours required to reach failure was 2.2 times that of the control sample.

In the manner of Example 1, using the appropriate halocompound and appropriate phosphinodithioic acid ammonium salt, additional compounds were prepared and tested as in Example 2. In some instances the resulting phosphinodithioic acid ester was insoluble in acetone at room temperature. The precipitate was then filtered off, washed with water to remove any ammonium halide salts, dried and recrystallized. The compounds and test results are described below.

EXAMPLE 3

Cyclohexylbromide was reacted with the ammonium salt of dicyclohexylphosphinodithioic acid to obtain cyclohexyldicyclohexylphosphinodithioate, m.p. 82°–85° C, which on testing lasted 1250 hours* longer than the control. The average number of hours required to reach failure was 3.5 times that of the control.

EXAMPLE 4

Methyl bromide was reacted with the ammonium salt of dicyclohexylphosphinodithioic acid to obtain methyl dicyclohexylphosphinodithioate, m.p. 75°–75.5° C, which on testing lasted 1500 hours* longer than the control. The average total number of hours required to each failure was 3.4 times that of the control.

EXAMPLE 5

1,10-Dibromodecane was reacted with two molecular equivalents of the ammonium salt of dicyclohexylphosphinodithioic acid to obtain 1,10-decamethylenebis(dicyclohexylphosphinodithioate), m.p. 83°–84° C, which on testing lasted 800 hours longer than the control. The total number of hours required to reach failure was 3.0 times that of the control.

EXAMPLE 6 n-Octyl bromide was reacted with the ammonium salt of dicyclohexylphosphinodithioic acid to obtain n-octyl dicyclohexylphosphinodithioate, a colorless viscous liquid, which on testing lasted 900 hours longer than the control. The total number of hours required to reach failure was 2.8 times that of the control.

EXAMPLE 7 n-Butyl bromide was reacted with the ammonium salt of dicyclohexylphosphinodithioic acid to obtain n-butyl dicyclohexylphosphinodithioate, a viscous liquid, b.p. 167°–175° C at 0.15 mm., which on testing lasted 900 hours longer than the control. The total number of hours required to reach failure was 2.8 times that of the control.

EXAMPLE 8

11-Methyldodecyl bromide was reacted with the ammonium salt of dicyclohexylphosphinodithioic acid to obtain isotridecyl dicyclohexylphosphinodithioate, a viscous colorless liquid, which on testing lasted 750 hours longer than the control. The total number of hours required to reach failure was 2.6 times that of the control.

EXAMPLE 9

Methylene dibromide was reacted with two molecular equivalents of the ammonium salt of dicyclohexylphosphinodithioic acid to obtain methylene bis(dicyclohexylphosphinodithioate), which on testing lasted 600 hours longer than the control. The total number of hours required to reach failure was 2.5 times that of the control.

EXAMPLE 10

Bis(2-bromoethyl) sulfide was reacted with two molecular equivalents of the ammonium salt of dicyclohexylphosphinodithioic acid to obtain 2,2'-thiodiethylene bis(dicyclohexylphosphinodithioate), which on testing lasted 600 hours longer than the control. The total number of hours required to reach failure was 2.5 times that of the control.

EXAMPLE 11

1,2-Dichloroethane was reacted with two molecular equivalents of the ammonium salt of dicyclohexylphosphinodithioic acid to prepare 1,2-ethylene bis(dicyclohexylphopshinodithioate), m.p. 200°–201° C, which on testing lasted 600 hours longer than the control. The total number of hours required to each failure was 2.2 times that of the control.

EXAMPLE 12

1,3-Dibromopropane was reacted with two molecular equivalents of the ammonium salt of dicyclohexylphosphinodithioic acid to obtain 1,3-propylenebis(dicyclohexylphosphinodithioate), m.p. 135°–136° C, which on testing lasted 450 hours longer than the control The total number of hours required to reach failure was 2.1 times that of the control.

EXAMPLE 13

2-Bromoethanol was reacted with the ammonium salt of dicyclohexylphosphinodithioic acid to obtain 2-hydroxyethyldicyclohexylphosphinodithioate, m.p. 82°–84° C, which on testing lasted 500 hours longer than the control. The total number of hours required to reach failure was 2.0 times that of the control.

EXAMPLE 14

2-Hydroxy-1,3-dibromopropane was reacted with two molecular equivalents of the ammonium salt of dicyclohexylphosphinodithioic acid to obtain 2-hydroxy-1,3-propylenebis-(dicyclohexylphosphinodithioate), m.p. 130°–132° C, which on testing lasted 450 hours longer than the control. The total number of hours required to reach failure was 2.0 times that of the control.

EXAMPLE 15

3,5-di-t-butyl-4-hydroxybenzyl bromide was reacted with the ammonium salt of dicyclohexylphosphinodithioic acid to obtain 3,5-di-t-butyl-4-hydroxybenzyl dicyclohexylphosphinodithioate, m.p. 129°–131° C, which on testing lasted 475 hours* longer than the control. The total number of hours required to reach failure was 1.9 times that of the control.

EXAMPLE 16

Benzyl bromide was reacted with the ammonium salt of dicyclohexylphosphinodithioic acid to obtain benzyl dicyclohexylphosphinodithioate, m.p. 107°14 108° C, which on testing lasted 350 hours longer than the control. The total number of hours required to reach failure was 1.9 times that of the control.

EXAMPLE 17 n-Butyl bromide was reacted with the ammonium salt of diisobutylphosphinodithioic acid to obtain n-butyl diisobutylphosphinodithioate, a colorless liquid, b.p. 97°–103° C at 0.05 mm. which on testing lasted 200 hours longer than the control. The total number of hours required to reach failure was 1.4 times that of the control.

EXAMPLE 18

2,6-Dimethyl-3-hydroxy-4-t-butylbenzyl bromide was reacted with the ammonium salt of dicyclohexylphosphinodithioic acid to obtain 2,6-dimethyl-3-hydroxy-4-t-butylbenzyl dicyclohexylphosphinodithioate, m.p. 113°–116° C, which on testing lasted 150 hours longer than the control. The total number of hours required to reach failure was 1.3 times that of the control.

EXAMPLE 19

1,4-Bis(bromomethyl)benzene was reacted with two molecular equivalents of the ammonium salt of dicyclohexylphosphinodithioic acid to obtain 1,4-xylylenebis (dicyclohexylphosphinodithioate), m.p. 242°–244° C, which on testing lasted 100 hours longer than the control. The total number of hours required to reach failure was 1.2 times that of the control.

We claim:

1. A polymeric composition stabilized against degradation by ultraviolet light by an effective amount of a compound of the formula:

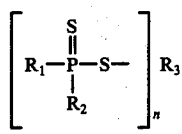

wherein $R_1$ and $R_2$ are selected from alkyl; cycloalkyl; alkyl substituted by hydroxy, alkoxy, cyano, chloro, bromo, or fluoro; aryl; aralkyl; aryl and aralkyl substituted by one or two lower alkyl, lower alkoxy, hydroxy, or halogen on the aryl moiety thereof; $n$ is 1 or 2; and, when $n$ is 1, $R_3$ is selected from alkyl; cycloalkyl; alkyl substituted by hydroxy, alkoxy, cyano, chloro, bromo, or fluoro; alkylthioalkyl; aralkyl; aryl; aralkylthioalkyl; and aralkyl, aryl, or aralkylthioalkyl substituted by one or two lower alkyl, lower alkoxy, hydroxy, or halogen on the aryl moiety thereof, and, when $n$ is 2, $R_3$ is selected from alkylene; hydroxyalkylene; oxybis and thiobis(alkylene); arylene; or arylene substituted by lower alkyl, lower alkoxy, hydroxy, or halogen.

2. A composition as defined in claim 1 wherein said polymeric composition is a polyolefin.

3. A composition as defined in claim 2 wherein said polyolefin is polypropylene.

4. A composition as defined in claim 1 wherein said light-stabilizing amount is about 0.1% to about 5% by weight of said compound on the weight of said polymeric composition.

5. A composition as defined in claim 1 wherein said compound has the formula:

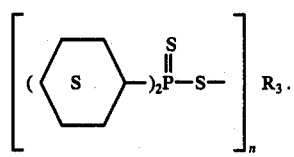

6. A composition as defined in claim 5 wherein said compound has the formula:

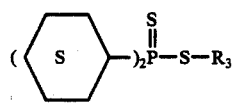

wherein $R_3$ is alkyl of 1 to 18 carbon atoms.

7. A composition as defined in claim 5 wherein said compound has the formula:

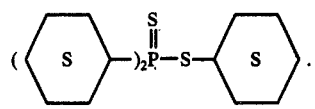

8. A composition as defined in claim 6 wherein said compound has the formula:

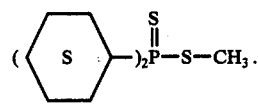

9. A composition as defined in claim 6 wherein said compound has the formula:

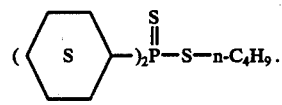

10. A composition as defined in claim 6 wherein said compound has the formula:

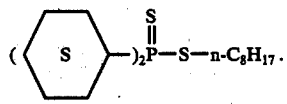

11. A composition as defined in claim 6 wherein said compound has the formula:

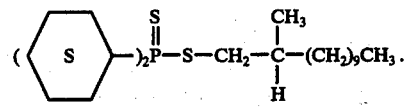

12. A composition as defined in claim 6 wherein said compound has the formula:

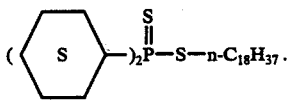

13. A composition as defined in claim 5 wherein said compound has the formula:

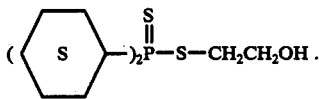

14. A composition as defined in claim 5 wherein said compound has the formula:

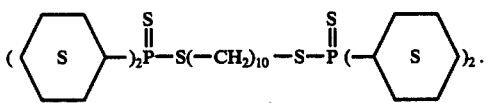

15. A composition as defined in claim 5 wherein said compound has the formula:

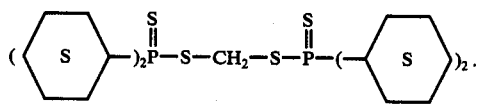

16. A composition as defined in claim 5 wherein said compound has the formula:

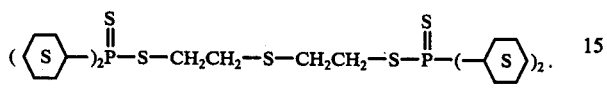

17. A composition as defined in claim 5 wherein said compound has the formula:

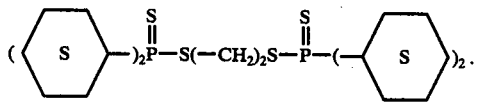

18. A composition as defined in claim 5 wherein said compound has the formula:

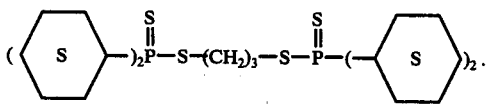

19. A composition as defined in claim 5 wherein said compound has the formula:

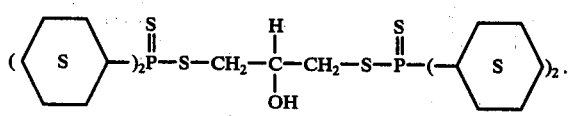

20. A composition as defined in claim 5 wherein said compound has the formula:

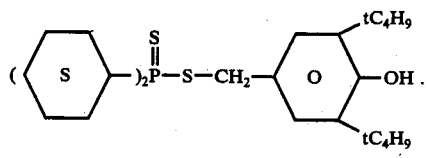

21. A composition as defined in claim 5 wherein said compound has the formula:

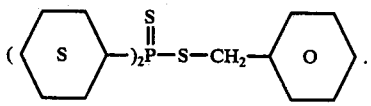

22. A composition as defined in claim 5 wherein said compound has the formula:

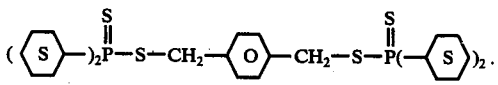

23. A composition as defined in claim 5 wherein said compound has the formula:

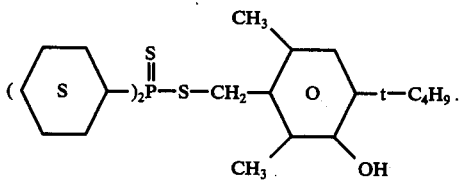

24. A composition as defined in claim 1 wherein said compound has the formula:

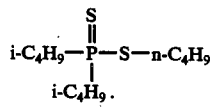

25. A composition as defined in claim 1 wherein $n$ is 1.

26. A composition as defined in claim 1 wherein $n$ is 2.

* * * * *